United States Patent [19]

Maurer et al.

[11] Patent Number: 4,882,320
[45] Date of Patent: Nov. 21, 1989

[54] PESTICIDAL PYRIMIDINYL (THIONO)(THIO)-PHOSPHATES

[75] Inventors: Fritz Maurer, Wuppertal; Benedikt Becker, Mettmann; Bernhard Homeyer, Leverkusen, all of Fed. Rep. of Germany

[73] Assignee: Bayer Aktiengesellschaft, Leverkusen, Fed. Rep. of Germany

[21] Appl. No.: 237,242

[22] Filed: Aug. 26, 1988

[30] Foreign Application Priority Data

Sep. 2, 1987 [DE] Fed. Rep. of Germany ....... 3729264

[51] Int. Cl.$^4$ .......................... A01N 57/16; C07F 9/65
[52] U.S. Cl. ......................................... 514/86; 544/243
[58] Field of Search ........................... 544/243; 546/81

[56] References Cited

U.S. PATENT DOCUMENTS

| | | | |
|---|---|---|---|
| 2,754,243 | 7/1956 | Gysin et al. | 514/86 |
| 3,309,371 | 3/1967 | Curry et al. | 544/243 X |
| 3,951,975 | 4/1976 | Hofer et al. | 544/243 |
| 4,155,999 | 5/1979 | Maurer et al. | 514/86 |

FOREIGN PATENT DOCUMENTS 3445465  6/1986  Fed. Rep. of Germany ........ 514/86

Primary Examiner—Mukund J. Shah
Assistant Examiner—Diana G. Rivers
Attorney, Agent, or Firm—Sprung Horn Kramer & Woods

[57] ABSTRACT

Pesticidally active pyrimidinyl (thiono)(thio)-phosphates of the formula

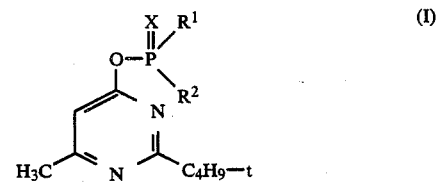

in which
$R^1$ stands for alkoxy,
$R^2$ stands for alkoxy or alkylthio and
X stands for oxygen or sulphur, with the proviso that the two radicals $R^1$ and $R^2$ are identical when they stand for alkoxy.

12 Claims, No Drawings

PESTICIDAL PYRIMIDINYL (THIONO)(THIO)-PHOSPHATES

The invention relates to new pyrimidinyl(thiono)-(thio)-phosphates, a process for their preparation and their use as pest combating agents, in particular as insecticides, acaricides and nematicides.

It has already been disclosed that certain pyrimidinyl(thiono) (thio)-phosphates, such as, for example O-ethyl S-n-propyl O-(2-isopropyl-6-methyl-pyrimidin-4-yl) thionothiophosphate and O,O-diethyl O-(2-methyl-6-tert.-butyl-pyrimidin-4-yl) thionophosphate, are active as pesticides (compare DE-OS (German Published Specification) No. 2,639,433; DE-OS (German Published Specification) No. 2,360,877). However, the action and the duration of action of these known compounds are not always completely satisfactory, in particular at low application rates or active compound concentrations.

New pyrimidinyl(thiono)(thio)-phosphates of the general formula (I)

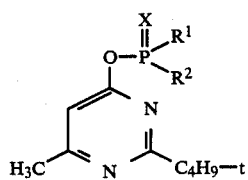

have now been found, in which
$R^1$ stands for alkoxy,
$R^2$ stands for alkoxy or alkylthio and
X stands for oxygen or sulphur,
with the proviso that the two radicals $R^1$ and $R^2$ are identical when they stand for alkoxy.

Furthermore, it has been found that the new pyrimidinyl(thiono)(thio)-phosphates of the formula (I) are obtained when 2-tert.-butyl-4-hydroxy-6-methyl-pyrimidine of the formula (II)

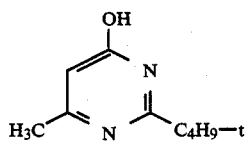

or the corresponding alkali metal salt, alkaline earth metal salt or ammonium salt is reacted with halides of the formula (III)

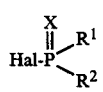

in which
$R^1$, $R^2$ and X have the abovementioned meaning and Hal stands for halogen, preferably chlorine or bromine, if appropriate in the presence of an acid-acceptor and if appropriate in the presence of a diluent.

The new pyrimidinyl(thiono)(thio)phosphates of the formula (I) are distinguished in an outstanding manner by a particularly high activity as pest-combating agents, in particular as insecticides, acaricides and nematicides.

The substances according to the invention thus represent a valuable enrichment of the art.

The term alkoxy in the definition of $R^1$ and $R^2$ in the general formulae is taken to mean straight-chain or branched alkoxy preferably having 1 to 6 carbon atoms, for example the following groups: methoxy, ethoxy, propoxy, butoxy and also their isomers, such as, for example, i-propoxy, i-, s- and tert.-butoxy. Particularly preferred alkoxy radicals $R^1$ and $R^2$ contain 1 to 4 carbon atoms. Methoxy-, ethoxy-, n-propoxy- and i-propoxy are particularly preferred, and methoxy and ethoxy are very particularly preferred.

The term alkylthio in the definition of $R^2$ in the general formulae is taken to mean straight-chain or branched alkylthio preferably having 1 to 6 carbon atoms, for example the following groups: methylthio-, ethylthio-, propylthio-, butylthio-, pentylthio and also their isomers, such as, for example, i-propylthio, i-, s-and tert.-butylthio, 1-methyl-butylthio, 2-methyl-butylthio-and 3-methylbutylthio. Particularly preferred alkylthio radicals $R^2$ contain 1 to 4 carbon atoms. Methylthio, ethylthio, n-, i-, s-propylthio and n-, i-, s- and tert.-butylthio are particularly preferred, and n-propylthio and s-butylthio are very particularly preferred.

Of the pyrimidinyl(thiono)(thio)-phosphates of the formula (I) according to the invention, those are preferred in which
$R^1$ stands for $C_1$-$C_4$-alkoxy,
$R^2$ stands for $C_1$-$C_4$-alkoxy and $C_1$-$C_4$-alkylthio and
X stands for oxygen or sulphur,
with the proviso that the two radicals $R^1$ and $R^2$ are identical when they stand for alkoxy.

Particularly preferred pyrimidinyl(thiono)(thio)phosphates of the formula (I) are those in which
$R^1$ stands for methoxy, ethoxy, n-propoxy and i-propoxy (preferably methoxy and ethoxy),
$R^2$ stands for methoxy, ethoxy, n-propoxy, i-propoxy, methylthio, ethylthio, n- and i-propylthio, n-, i-, s- and tert.-butylthio (preferably methoxy, ethoxy, n-propylthio and s-butylthio) and
X stands for oxygen or sulphur,
with the proviso that the two radicals $R^1$ and $R^2$ are identical when they stand for alkoxy.

The preferred definitions given for the compounds of the formula (I) also apply to the starting compounds of the formula (III).

The following compounds of the formula (I)

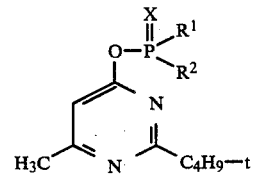

may be mentioned individually in addition to the compounds mentioned in the preparation examples:

TABLE 1

| X | $R^1$ | $R^2$ |
|---|---|---|
| S | $OC_3H_7$-n | $OC_3H_7$-n |
| S | $OC_3H_7$-i | $OC_3H_7$-i |
| O | $OC_2H_5$ | $OC_2H_5$ |

If, for example, O,O-diethyl chlorophosphate and 2-tert.-butyl-4-hydroxy-4-hydroxy-6-methyl-pyrimidine are used as starting materials for the process according to the invention, then the appropriate reaction can be outlined by the following equation:

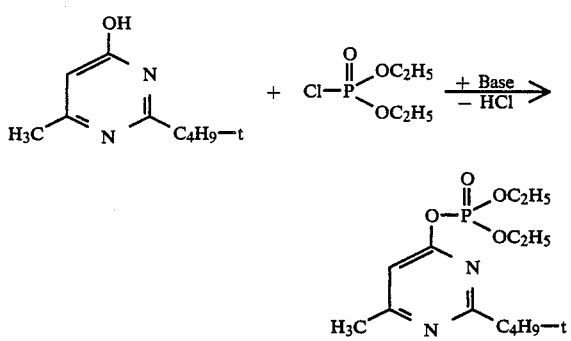

Formula (II) provides a definition of the 2-tert.-butyl-4-hydroxy-6-methyl-pyrimidine or the corresponding alkali metal salt, alkaline earth metal salt or ammonium salt to be employed in the process according to the invention as the starting material for the preparation of the new compounds of the formula (I). Sodium salts, potassium salts or calcium salts are preferably employed as the alkali metal salts or alkaline earth metal salts.

2-tert.-Butyl-4-hydroxy-6-methyl-pyrimidine is known (see J. Chem. Soc. (London) 1963, 5652).

Formula (III) provides a definition of the halides additionally to be employed as starting materials. In this formula, $R^1$, $R^2$ and X stand for those radicals which are given in the definition in formula (I). Hal in this formula stands for halogen, such as chlorine or bromine in particular.

The compounds of the formula (III) are known.

Examples of the halides of the formula (III) which may be mentioned are: O,O-dimethyl, O,O-diethyl, O,O-di-n-propyl or O,O-diisopropyl chlorophosphate and also the corresponding thiono derivatives, and furthermore O-methyl S-methyl, O-methyl S-ethyl, O-methyl S-n-propyl, O-methyl S-isopropyl, O-methyl S-n-butyl, O-methyl S-isobutyl, O-methyl S-sec.-butyl, O-methyl S-tert.-butyl, O-ethyl S-methyl, O-ethyl S-ethyl, O-ethyl S-n-propyl, O-ethyl S-isopropyl, O-ethyl S-n-butyl, O-ethyl S-iso-butyl, O-ethyl S-sec.-butyl or O-ethyl S-tert.-butyl chlorothiophosphate and also the corresponding thiono derivatives.

The process according to the invention for the preparation of the new pyrimidin-4-yl-thionophosphates of the formula (I) is preferably carried out using diluents. Suitable diluents are practically all inert organic solvents.

In particular, these include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene, o-dichlorobenzene, ethers such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and n-methylpyrrolidone, and also dimethyl sulphoxide, tetramethylenesulphone and hexamethylphosphoric triamide.

If desired, the process can be carried out in the presence of acid-acceptors. Acid-acceptors which can be used are all customary acid-binding agents. Particularly suitable are alkali metal carbonates, such as sodium carbonate and potassium carbonate, alkali metal hydrides, such as sodium hydride, and furthermore aliphatic, aromatic or heterocyclic amines, for example triethylamine, trimethylamine, dimethylaniline, dimethylbenzylamine and pyridine.

The process according to the invention is generally carried out at temperatures between 0° C. and 100° C. The range between 20° C. and 80° C. is preferred. The reactions are generally carried out at atmospheric pressure.

For carrying out the process according to the invention, the starting substances are usually employed in approximately equimolar amounts. An excess of one or the other reaction component has no substantial advantages. The reaction is generally carried out in a suitable diluent in the presence of an acid acceptor and the reaction mixture is stirred for several hours at the required temperature. An organic solvent, for example toluene, is then added and the organic phase is worked up as customary by washing, drying and removing the solvent by distillation. The new compounds are produced in the form of oils which cannot be distilled without partial decomposition, but are freed from the last volatile constituents by so-called "incipient distillation", that is by relatively long heating under reduced pressure to moderately raised temperatures, and are purified in this manner. The refractive index is used for their characterization.

The active compounds are suitable for combating animal pests, preferably arthropods and nematodes, in particular insects and arachnida, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcello scaber.* From the order of the Diplopoda, for example, *Blaniulus guttulatus.* From the order of the Chilopoda, for example, *Geophilus carpophagus* and *Scutigera spec..* From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma Lanigerum, Hyalopterus arundinis, Macrosiphum avenae, Myzus* spp., *Phorodon humuli, Rhopalosiphum padi,*

Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossyiella, Bupalus piniarius, Cheimatobia brumata, Lithocolletis blancardella, Hyponomeuta padella, Plutella maculipennis, Malacosoma neustria, Euproctis, tis chrysorrhoea, Lymantria spp. Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia Litura,* Spodoptera spp., *Trichlophusia ni, Carprocapsa pomonella,* Pieris spp., Chilo spp., *Pyrausta nubilalis, Ephestia kuehniella, Galleria mellonella, Tineola bisselliella, Tinea pellionella, Hofmannophila pseudospretella Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae.* Diabrotica spp., *Psylliodes chrysocephala, Epilachna varive stis,* Atomarb spp., *Oryzaeophilus surinamensis,* Antho nomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololecus, Gibbium psylloides,* Tribolium spp. *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit.* Phorbia spp., *Pegomyia hyoscyami, Ceratitis capitata, Dacus oleae* and *Tipula paludos.* From the order of the Siphonaptera, for example, *Xneopsylla cheopis* and Ceratophyllus spp. From the order of the Arachnida, for example, *Scorpia maurus and Latrodectus mactans.* From the order of the Acarina, for example, *Acarus siro,* Argas spp., Ornithodoros spp., *Dermanyssus gallinae, Eiophyes ribis, Phyllocotruta oleivora,* Boophilus spp., Rhipicephalulus spp., Amblyomma spp., Hyalomma spp., Ixodes spp., Psoroptes spp., Choriopetes spp., Sacroptes spp., Tarsonemus spp., *Bryobia praetiosa,* Panonychus spp. and Tetranychus spp.

The phtoparasitic nematodes include Pratylenchus spp., *Radopholus similis, Ditylenchus dipsaci, Tylenchulus semipenetrans,* Heterodera spp., Meloiodogyne spp., Aphelenchoides spp., Longidorus spp., Xiphinema spp. and Trichodorus spp.

The active compounds according to the invention are distinguished by an outstanding insecticidal activity. Thus, in particular, the long-lasting action against soil insects, such as, for example, *Phorbia antiqua,* the outstanding action against nematodes, such as, for example, *Meliodogyne incognita,* and also the outstanding action against insects which are harmful to plants, such as, for example, Tetranychus species, can be mentioned.

Moreover, some of the active compounds according to the invention also show an action against hygiene pests and stored product pests.

Depending on their particular physical and/or chemical properties, the active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, and furthermore into formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and-/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorilonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds can be present in their commercially available formulations and in the use forms, prepared from these formulations, as a mixture with other active compounds, such as insecticides, baits, sterilizing agents, acaricides, nematicides, fungicids, growth-regulating substances or herbicides. The insecticides include, for example, phosphates, carbamates, carboxylates, chlorinated hydrocarbons, phenylureas, substances produced by microorganisms.

The active compounds can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The preparation and the use of the active compounds according to the invention is illustrated by the following examples.

In the present test, all percentage data signify percentages by weight, unless otherwise stated.

Preparation Examples

EXAMPLE 1

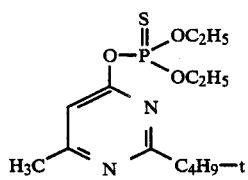

A mixture of 16.6 g (0.1 mol) of 4-hydroxy-6-methyl-2-tert.-butyl-pyrimidine, 20.7 g (0.15 mol) of potassium carbonate, 19 g (0.1 mol) of O,O-diethyl chlorothiophosphate and 100 ml of acetonitrile is stirred at 50° C. for 2 hours. The mixture is then cooled to 20° C., 400 ml of toluene are added and the mixture is shaken twice using ml of water each time. The organic phase is separated off, dried over sodium sulfate and evaporated in vacuo.

After incipient distillation at 80° C. in high vacuum, 28.9 g (91% of theory) of O,O-diethyl O-(6-methyl-2-tert.-butyl-pyrimidin-4-yl) thionophosphate remain in the form of a pale yellow oil of refractive index $n_D^{21}$: 1.4997.

The final products of the formula (I)

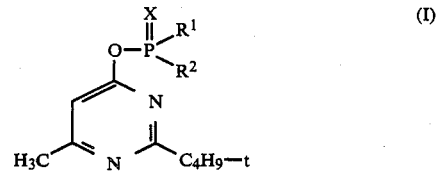

shown below are obtained in an analogous manner to Example 1 and with consideration for the instructions in the description of the process according to the invention:

TABLE 2

| Example No. | X | R$^1$ | R$^2$ | Refractive index $n_D^{21}$ |
| --- | --- | --- | --- | --- |
| 2 | S | OC$_2$H$_5$ | SC$_3$H$_7$-n | 1.5324 |
| 3 | S | OCH$_3$ | OCH$_3$ | 1.5008 |
| 4 | O | OC$_2$H$_5$ | SC$_3$H$_7$-n | 1.5070 |
| 5 | O | OC$_2$H$_5$ | SC$_4$H$_9$-s | 1.5043 |
| 6 | S | OC$_2$H$_5$ | SC$_4$H$_9$-s | 1.5272 |

Use Examples

The compounds shown below are used as comparison substances in some of the following use examples:

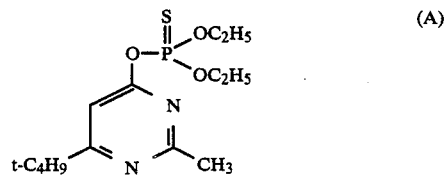

O,O-Diethyl O-(2-methyl-6-tert.-butyl-pyrimidin-4-yl) thionophosphate (known from DE-OS (German Published Specification) No. 2,639,433),

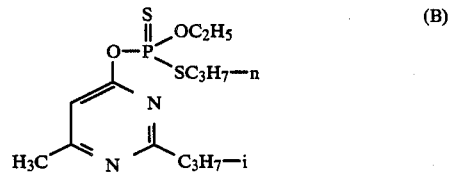

O-ethyl S-n-propyl O-(2-isopropyl-6-methyl-pyrimidin-4-yl) thionothiophosphate (known from DE-OS (German Published Specification) No. 2,360,877).

EXAMPLE A

Critical concentration test/soil insects

Test insect: *Phorbia antiqua* maggots (in the soil)
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/l), being decisive. The soil is filled into pots and the pots are left to stand at room temperature.

After 24 hours, the test animals are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, the compounds of Examples (1), (2) and (3) showed a degree of destruction of 100% at a concentration of 2.5 ppm, for example, whereas the comparison substance (A) showed no destruction (0%) at the same concentration.

EXAMPLE B

Critical concentration test/nematodes

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil which is heavily infested with the test nematodes. The concentration of the active compound in the preparation is of practically no importance here, only the amount of active compound per unit volume of soil, which is given in ppm, being decisive. The treated soil is filled into pots, lettuce is sown and the pots are kept at a greenhouse temperature of 27° C.

After four weeks, the lettuce roots are examined for infestation with nematodes (root galls), and the degree of effectiveness of the active compound is determined in %. The degree of effectiveness is 100% if infestation is completely avoided and is 0% if the infestation is just as high as in the case of the control plants in untreated soil which has been infested in the same manner.

In this test, for example, the compound (2) showed a degree of destruction of 100% at a concentration of 10 ppm, for example, whereas the comparison compound (B) showed no destruction (0%) at the same concentration.

EXAMPLE C

Tetranychus test (resistant)

Solvent: 3 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with the common spider mite or bean spider mite (*Tetranychus urticae*) in all stages of development are treated by being dipped into the preparation of the active compound of the desired concentration.

After the desired time, the destruction in % is determined. 100% means that all the spider mites have been killed; 0% means that none of the spider mites have been killed.

In this test, for example, the compounds of Examples (4), (5) and (6) showed a degree of destruction of 98% and the compound of Example (2) showed a degree of destruction of 100% after 2 days at a concentration of 0.1%, for example, whereas the comparison compound (A) showed no destruction (0%) after 2 days at the same concentration.

It will be appreciated that the instant specification and claims are set forth by way of illustration and not limitation, and that various modifications and changes may be made without departing from the spirit and scope of the present invention.

What is claimed is:

1. A pyrimidinyl(thiono)(thio)-phosphate of the formula

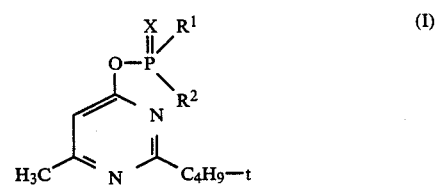

in which
$R^1$ stands for $C_1$–$C_4$ alkoxy,
$R^2$ stands for alkoxy or $C_1$–$C_4$ alkylthio and
X stands for oxygen or sulphur,
with the proviso that the two radicals $R^1$ and $R^2$ are identical when they stand for alkoxy.

2. A compound according to claim 1, in which
$R^1$ stands for methoxy, ethoxy, n-propoxy and i-propoxy,
$R^2$ stands for methoxy, ethoxy, n-propoxy, i-propoxy, methylthio, ethylthio, n- and i-propylthio, n-, i-, s- and tert.-butylthio and
X stands for oxygen or sulphur,
with the proviso that the two radicals $R^1$ and $R^2$ are identical when they stand for alkoxy.

3. A compound according to claim 1, in which
$R^1$ stands for methoxy or ethoxy,
$R^2$ stands for methoxy, ethoxy, n-propylthio or s-butylthio and
X stands for oxygen or sulphur,
with the proviso that the two radicals $R^1$ and $R^2$ are identical when they stand for alkoxy.

4. A compound according to claim 1, wherein such compound is O,O-diethyl O-(6-methyl-2-tert.-butyl-pyrimidin-4-yl) thionophosphate of the formula

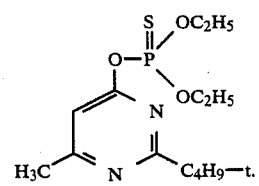

5. A compound according to claim 1, wherein such compound is O-ethyl S-n-propyl O-(6-methyl-2-tert.-butyl-pyrimidin-4-yl) thionothiophosphate of the formula

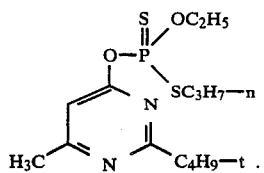

6. A compound according to claim 1, wherein such compound is O,O-dimethyl O-(6-methyl-2-tert.-butyl-pyrimidin-4-yl) thionophosphate of the formula

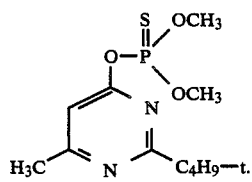

7. A compound according to claim 1, wherein such compound is O-ethyl S-n-propyl O-(6-methyl-2-tert.-butyl-pyrimidin-4-yl) thiophosphate of the formula

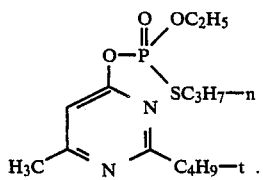

8. A compound according to claim 1, wherein such compound is O-ethyl S-s-propyl O-(6-methyl-2-tert-butyl-pyrimidin-4-yl) thiophosphate of the formula

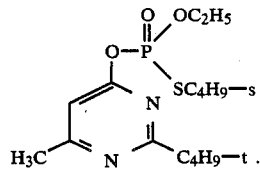

9. A compound according to claim 1, wherein such compound is O-ethyl S-s-butyl O-(6-methyl-2-tert.-butyl-pyrimidin-4-yl) thiophosphate of the formula

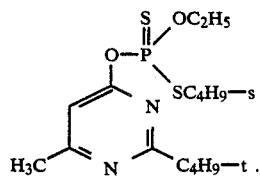

10. An insecticidal, acaricidal or nematocidal composition comprising an insecticidally, acaricidally or nematicidally effective amount of a compound according to claim 1 and a diluent.

11. A method of combating insects, acarids or nematodes which comprises applying to such insects, acarids, nematodes or habitat thereof an insecticidally, acaricidally or nematicidally effective amount of a compound according to claim 1.

12. The method according to claim 12, wherein such compound is
O,O-diethyl O-(6-methyl-2-tert.-butyl-pyrimidin-4-yl) thionophosphate,
O-ethyl S-n-propyl O-(6-methyl-2-tert.-butyl-pyrimidin-4-yl) thionothiophosphate,
O,O-dimethyl O-(6-methyl-2-tert.-butyl-pyrimidin-4-yl) thionophosphate,
O-ethyl S-n-propyl O-(6-methyl-2-tert.-butyl-pyrimidin-4-yl) thiophosphate,
O-ethyl S-s-butyl O-(6-methyl-2-tert.-butyl-pyrimidin-4-yl) thiophosphate, or
O-ethyl S-s-butyl O-(6-methyl-2-tert.-butyl-pyrimidin-4-yl) thionothiophosphate.

* * * * *

UNITED STATES PATENT AND TRADEMARK OFFICE
CERTIFICATE OF CORRECTION

PATENT NO. : 4,882,320

DATED : November 21, 1989

INVENTOR(S) : Maurer et al.

It is certified that error appears in the above-identified patent and that said Letters Patent is hereby corrected as shown below:

Col. 10, claim 1 line 28    After " for " add -- $C_1$-$C_4$ --

Col. 11, claim 8 line 44    Delete " S-s-propyl " and substitute -- S-s-butyl --

Col. 12, claim 9 line 12    Delete " thiophosphate " and substitute -- thionothiophosphate --

Col. 12, claim 10 line 25   After " claim " insert -- 1 --

Col. 12, claim 12 line 31   Delete " claim 12 " and substitute -- claim 11 --

Signed and Sealed this

Twenty-first Day of May, 1991

Attest:

HARRY F. MANBECK, JR.

Attesting Officer

Commissioner of Patents and Trademarks